United States Patent [19]

Ohno

[11] Patent Number: 4,468,819
[45] Date of Patent: Sep. 4, 1984

[54] EYE GOGGLES HAVING IMPROVED NOSE STRAP

[76] Inventor: Kaisaku Ohno, c/o Ohno Plastic Kogyo Kabushiki Kaisha, 3-16, Ukima 1-Chome, Kita-ku, Tokyo, Japan

[21] Appl. No.: 300,599
[22] Filed: Sep. 9, 1981
[51] Int. Cl.³ .............................................. A61F 9/02
[52] U.S. Cl. .......................................... 2/430; 2/445; 351/43; 351/128
[58] Field of Search .................. 2/428, 429, 430, 445, 2/446, 439; 351/43, 126–128, 133

[56] References Cited

U.S. PATENT DOCUMENTS

| 2,737,659 | 3/1956 | Glidden | 2/428 |
| 4,264,987 | 5/1981 | Runckel | 2/445 X |
| 4,286,340 | 9/1981 | Lathrop | 2/430 |

FOREIGN PATENT DOCUMENTS

| 2923798 | 12/1979 | Fed. Rep. of Germany | 351/43 |
| 1374010 | 8/1964 | France | 351/43 |
| 0131114 | 9/1960 | U.S.S.R. | 351/43 |

Primary Examiner—Peter P. Nerbun
Attorney, Agent, or Firm—Lowe, King, Price & Becker

[57] ABSTRACT

Two identical eye pieces are interconnected by a flexible nose strap. Each eye piece is formed from a single piece of plastic material for improved strength and includes a frame and an outwardly domed transparent hood. The hood includes a central lens portion and a side portion which extends laterally from the lens portion to the outer end of the frame. The lens portion is formed by a flat outer surface and a curved inner surface to permit the focal length to remain unchanged whether the eye goggles are used under or above water. The frame is provided with a connecting member engaging with the nose strap. The nose strap is formed with longitudinally spaced stops selectively engaging the connecting member. The longitudinal spacings between the stops on one side of the nose strap differ from those between the stops on the other side to obtain precision distance adjustment between the eye pieces.

5 Claims, 20 Drawing Figures

EYE GOGGLES HAVING IMPROVED NOSE STRAP

BACKGROUND OF THE INVENTION

The present invention relates to eye goggles worn to protect a wearer's eyes from water, particles or the like.

Conventional eye goggles comprise a pair of identical eye pieces interconnected by a flexible nose strap. Each eye piece includes a transparent lens portion secured within an inner periphery of a frame. The lens portion is generally circular, so that when an optical axis thereof is aligned with the line of sight the wearer's peripheral vision is severely restricted. Furthermore, the nose strap of conventional eye goggles is formed with equally longitudinally spaced apart stops. The number of possible combinations of this stop spacing arrangement is not sufficient to provide precision adjustment of the spacing between the eye pieces according to the wearer's facial contours.

SUMMARY OF THE INVENTION

The present invention eliminates these problems and comprises an eye piece having an integrally formed body of transparent material. The body includes a relatively stiff frame dimensioned to fit around an eye socket of the wearer and a generally dome shaped ovaloid transparent hood which is formed integrally with the frame and extends outwardly from the inner periphery thereof. A connecting member is attached to the inner end of each eye piece to engage a flexible nose strap so that the eye pieces are interconnected at a desired distance apart. The hood includes a lens portion and a side portion which is at an angle to the lens portion. The lens portion is formed by a flat outer surface and a curved inner surface and the side portion extends laterally from the lens portion to a point adjacent the outer end of the eye piece, for improved peripheral vision. Furthermore, the flat outer surface of the lens prevents the optical power thereof from departing from a normal value. This is advantageous for swimmers wearing the eye goggles in that the same focal length both under and above water is maintained.

A flexible sealing pad is secured to the inner side of the frame to contact the face of the wearer so as to provide an underwater seal around the eye socket. A flexible strap is secured to the outer end of the frame to extend around the back of the wearer's head to hold the eye pieces in proper position.

The nose strap comprises plural stops which are longitudinally spaced apart at least two different distances from each other for selectively engaging with the connecting member to hold the eye pieces in position at a desired distance part from each other. Because of the different spacings between individual stops, it allows a greater freedom with which any two of the stops may be used to engage the connecting means and a finer adjustment than is available with the prior art eye goggles.

A further feature of the invention is that since each eye piece is formed from a single piece of material, greater structural integrity is achieved.

BRIEF DESCRIPTION OF THE DRAWINGS

These and other features and advantages of the present invention will become apparent from the following detailed description which is given by way of example with reference to the accompanying drawings, in which.

DETAILED DESCRIPTION

Figure 1:
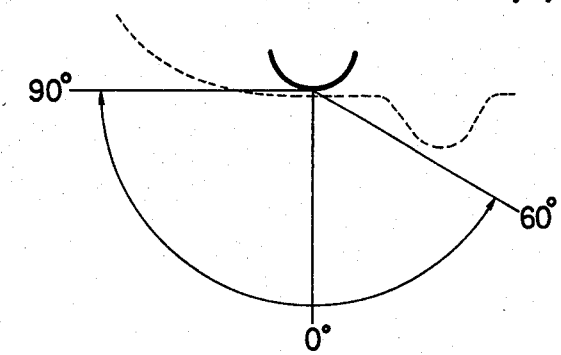
FIG. 1 is a sketch illustrating the natural human vision in plan of a right eye when no eye goggles are worn.
Figure 2:
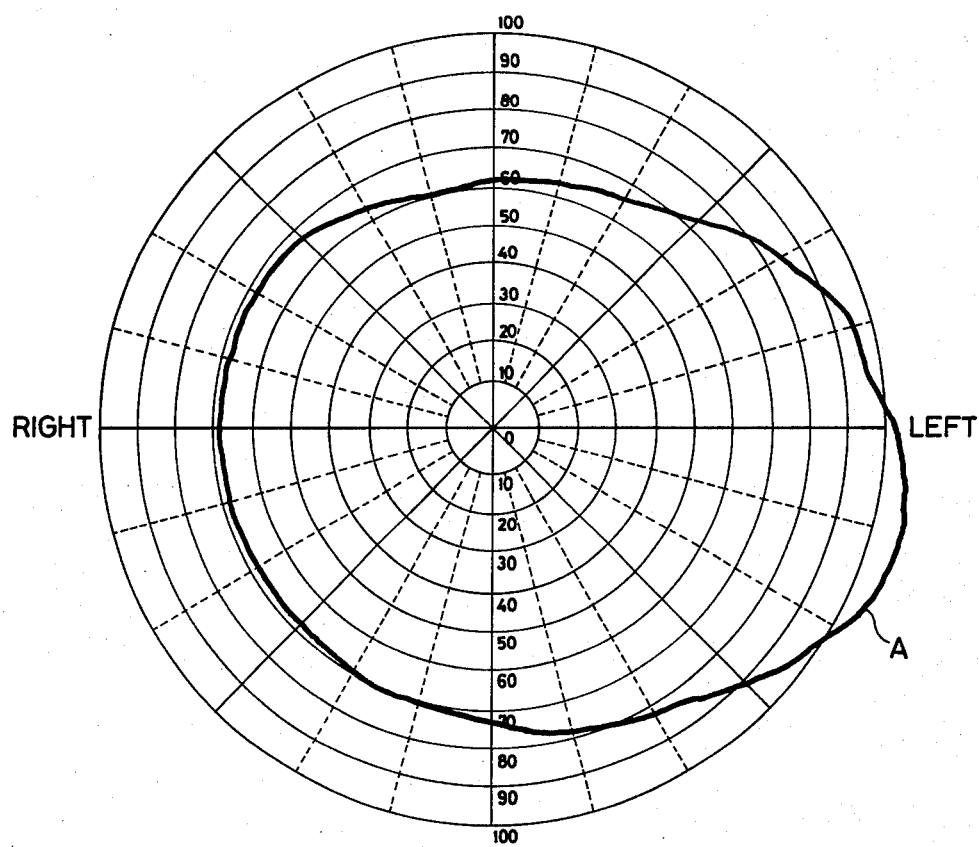
FIG. 2 is an illustration of the detail of the human vision of a left eye when the line of sight extends normal to the sheet.

Before going into the detail of the present invention, reference is first made to FIGS. 1 and 2. The field of vision of a human eye is usually limited to within a range from about 60 degrees to the line of sight on one side, as hindered by the nose indicated by broken lines, to about 90 degrees thereto on the other side. This is more specifically shown in FIG. 2 that the field of vision of a left eye, as indicated by a solid line A when the line of sight is pointing in a direction away from the rear to the front side of the sheet, extends to 70 degrees to the right, upper and lower sides and to 100 degrees to the left.

Figure 3A:
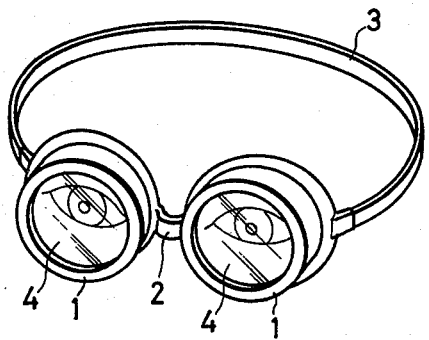
FIGS. 3a and 3b are schematic illustrations of a prior art eye goggles.
Figure 3B:
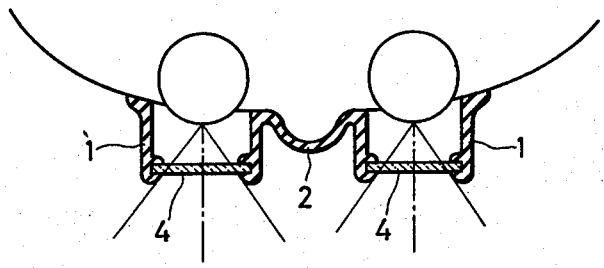

FIGS. 3a and 3b illustrate prior art eye goggles to be worn by swimmers, skiers or by workers to protect their eyes. These eye goggles are made up of two identical eye pieces 1, 1 interconnected by a nose strap 2. A flexible band 3 is provided to fit around the back of the wearer's head to hold the goggles in position. Each eye piece 1 is provided with a circular lens portion 4 having an optical axis aligned with the line of sight. Therefore, the field of vision of the wearer is severely limited compared with the natural field of vision mentioned in connection with FIGS. 1 and 2. The wearer thus needs to turn around his face to look sideways.

With eye goggles of the type wherein the eye pieces are interconnected by a nose strap, the latter is preferably made so that it allows adjustment of the spacing between the eye pieces according to the individual wearers.

Figure 4:
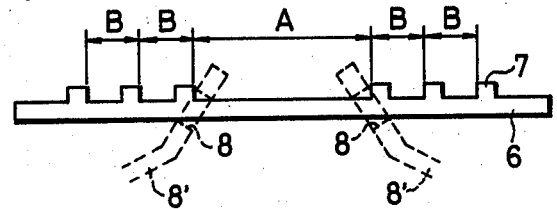
FIGS. 4 and 5 are illustrations of the nose strap of the prior art eye goggles of FIG. 3a showing stops for interconnecting the eye pieces at different distances.
Figure 5:
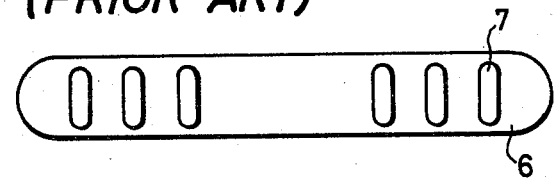
Figure 6:
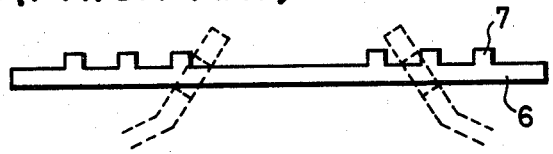
FIGS. 6 to 10 are illustrations of the nose strap showing different combinations of the stops of the nose strap of FIG. 4 being used for interconnecting the eye pieces.
Figure 7A:
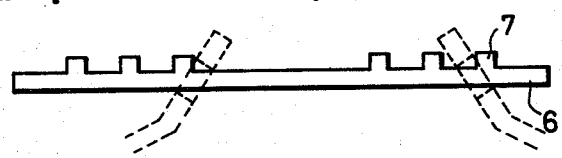
Figure 7B:
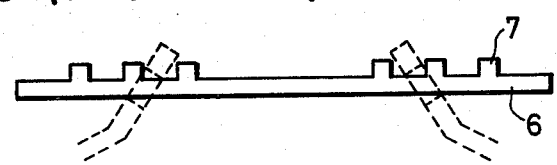
Figure 8:
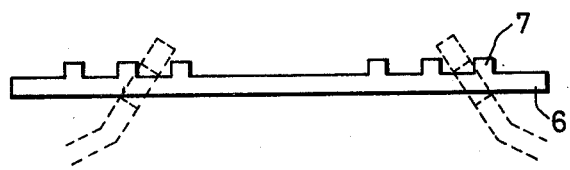
Figure 9:
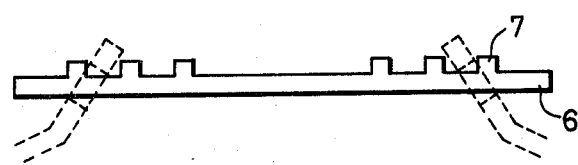
Figure 10:
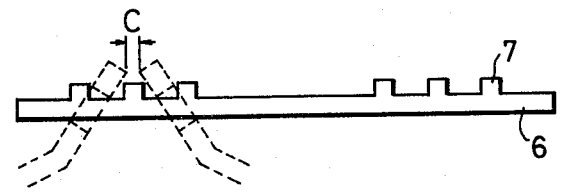

For this reason, conventional eye goggles are provided with an adjustable nose strap as shown in FIGS. 4 and 5. The nose strap of the adjustable type shown at 6 is threaded through holes 8, 8 of lugs 8', 8' fitted to the inner sides of the eye pieces and held in place by one of stops 7 which are spaced apart longitudinally of the strap on each side of the center thereof. Stops 7 are spaced at equal intervals B on each side and those on one side is spaced a distance A from those on the other side. Adjustment is achieved in discrete steps by different combinations of stops. Because of the equal interval B, however, the distances that can be chosen from among the possible combinations is six in the illustrated prior art embodiment. More specifically, the distance A+B is shown in FIG. 6; the distance A+2B in FIGS. 7a and 7b; the distance A+3B in FIG. 8; the distance A+4B; and the distance 2B minus the longitudinal extent C of the stop 7 in FIG. 10. If A=17 mm, B=4.5 mm and C=1.5 mm, the the available distances are 7.5 mm, 14 mm, 18.5 mm, 23 mm, 27.5 mm and 32 mm. Thus it is difficult for the wearer to achieve fine distance adjustments to snugly fit the eye goggles to his specific needs to keep water out when swimming or to align the optical axis of each lens with the line of sight. Misalignment of the optical axes might eventually cause a loss of sight if it exceeds 4 millimeters.

The present invention provides improved eye goggles which obviate the above-mentioned problem.

Figure 11:
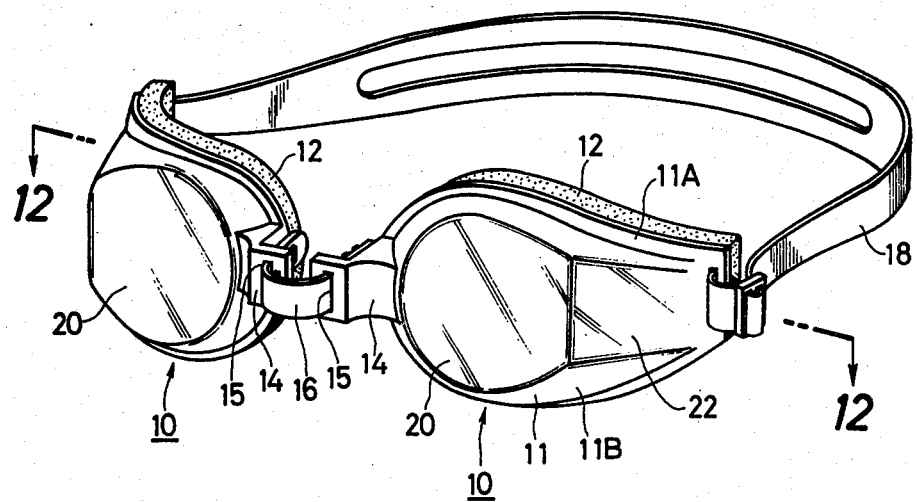
FIG. 11 is an illustration of a perspective view of eye goggles of the invention.
Figure 12:
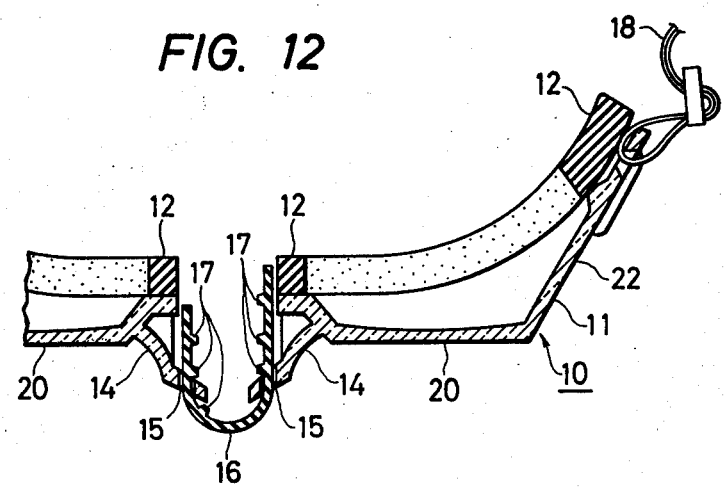
FIG. 12 is an illustration of a cross-sectional view taken along the lines 12—12 of FIG. 11.

FIG. 11 is an illustration of a preferred embodiment of the present invention. The eye goggles of the invention comprise a pair of identical eye pieces 10 formed of plastic material. Each eye piece 10 comprises a relatively rigid frame 11A. Pad 12 of a soft material (e.g. sponge) is fitted over the inner surface of frame 11A and is secured thereto by a suitable adhesive. As seen in FIG. 12, the pad 12 is relatively thick so that when the goggles are in place over the eyes of the wearer, the pad will deform to follow the contours of the wearer's face around the eye socket to form a seal. A transparent, generally dome shaped hood 11 has a peripheral edge is secured to frame 11A. Preferably, frame 11A and hood 11 are integrally molded from a single piece of plastic material. Frame 11A is formed integrally with a lug 14 on the inner end thereof projecting outwardly from the frame, as shown in FIG. 12. Lug 14 is formed with a slot 15 through which a nose strap 16 of the present invention is threaded and held in place by stops 17 described in greater detail below. A flexible band 18 is connected to the outer end of eye piece 10 and encircles the wearer's head to hold the eye pieces in position surrounding the eye.

Figure 13:
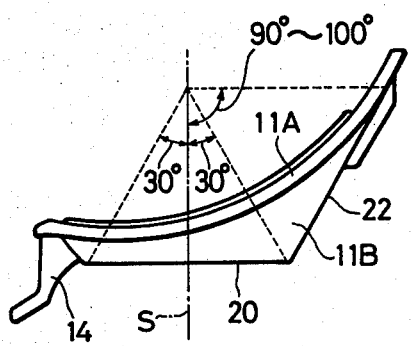
FIG. 13 is an illustration in a plan view of the left eye piece of the eye goggles of the invention.
Figure 14:
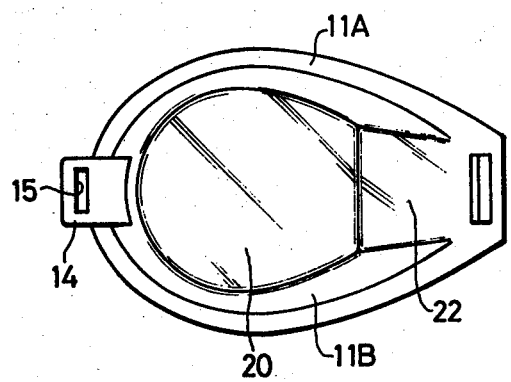
FIG. 14 is an illustration in a front view of the left eye piece of the invention.
Figure 15:
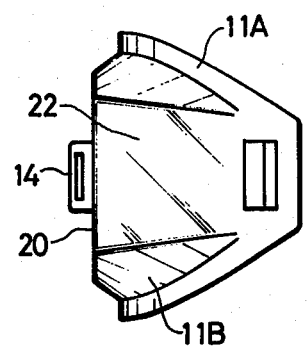
FIG. 15 is an illustration in a side view of the left eye piece of the invention.

Transparent hood 11 includes a wall 11B of ovaloid shape having a central lens portion 20 and a flat side portion 22 at an inclined angle to the lens portion as seen in FIGS. 13 to 15. While side portion 22 is shown and described as a flat surface, this portion could also be formed into a curved face as well. Lens portion 20 has an aperture that allows a viewing angle of 30 degrees on the inner side of line of sight S and a viewing angle of 30 degrees on the outer side thereof; side transparent portion 22 provides an additional peripheral viewing angle of about 70 degrees so that the wearer is given a maximum viewing angle of 100 degrees to the line of sight as seen in FIG. 13. According to a further feature of the invention, lens portion 20 has a curved inner surface and a flat outer surface so that the optical power remains unchanged whether used under or above water.

Figure 16:
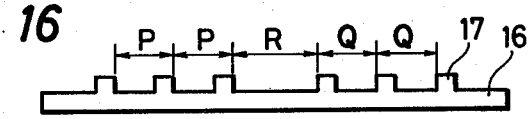
FIGS. 16, 17 and 18 are illustrations of the nose strap of the present invention.
Figure 17:
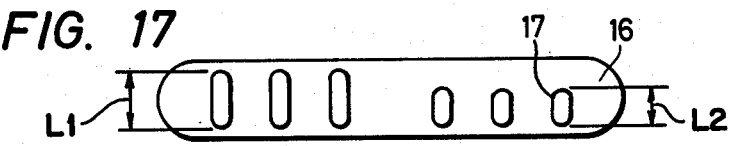
Figure 18:
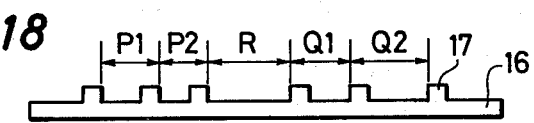

According to the invention, flexible nose strap 16 is formed of a pliable material such as rubber and provided with longitudinally spaced apart stops 17, six in number, as illustrated in FIGS. 16, 17 and 18. In FIGS. 16 and 17, the stops which are arranged on the left side of the strap 16 are spaced a distance P and those on the right side are individually spaced a distance Q greater than P and further spaced a distance R from those on the left side. In FIG. 18 the stops on the left side are spaced at unequally distances P1 and P2, and those on the right side are spaced unequally at distances Q1 and Q2.

By threading nose strap 16 through holes 15 of lugs 14, eye pieces 10 can be adjustably spaced at a desired distance determined by one of eleven different combinations of stops 17 that engage holes 15. More specifically, with reference to the embodiment of FIGS. 16, 17, the distance between eye pieces 10 can be selected from the following combinations: R, (R+Q), (R+2Q), (R+P), (R+2P), (R+P+Q), (R+P+2Q), (R+2P+Q), (R+2P+2Q), (2P minus the longitudinal extent of the stop) and (2Q minus the longitudinal extent of the stop). Therefore, if R=7 mm, P=4 mm and Q=5 mm and if each stop has a longitudinal extent of 1.5 mm, the selectable distances are 6.5 mm, 7 mm, 8.5 mm, 11 mm, 12 mm, 15 mm, 16 mm, 17 mm, 20 mm, 21 mm and 25 mm with an increment of less than 4 mm. The nose strap of the invention thus allows finer distance adjustment between eye pieces 10 as compared with the prior art nose strap described above. In the case of FIG. 18, a greater number of combinations of stops and a finer adjustment is possible.

A further fine adjustment could be obtained by dimensioning the longitudinal extent of each stop and spacing between them to have mutually different values. For example, the stops formed on the left hand side of strap 16 can be of length L1 while the straps on the right side of the strap can be of length L2, where L1≠L2 (see FIG. 17). The feature of having projection 17 of different length in this manner enables improved precisional height adjustment of one eyepiece relative to the other eyepiece to occur to accommodate facial contours of the individual wearer.

In the foregoing description, stops 17 of the strap 16 are shaped to form projections on one surface of the strap. However, stops 17 could be of any configuration so long as they serve to engage holes 15 or alternatively, the stops may be in the form of engaging holes or notches with lugs 14 each provided with a projecting element for engagement therewith.

While the foregoing description shows only preferred embodiments of the invention, various modifications and alterations of the present invention will be apparent to those skilled in the art without departing from the scope of the invention which is defined by the appended claims. Therefore, the embodiments shown and described are only illustrative, not restrictive.

What is claimed is:

1. Eye goggles for use in swimming or the like comprising a pair of separate eye pieces, a flexible nose strap interconnecting said eye pieces, each eye piece comprising an integrally formed body of a transparent material, said body comprising a relatively stiff frame dimensioned to fit around an eye socket of the wearer and a generally dome shaped ovaloid transparent hood formed integrally with said frame and extending outwardly from the inner periphery of said frame, said hood including a lens portion and a side portion inclined with respect to said lens portion, said lens portion including a flat outer surface and a curved inner surface and said side portion extending laterally from said inner lens portion to a point adjacent an outer end of said frame; connecting means attached to an inner end of said frame for engaging said nose strap; a flexible sealing pad formed on an inner side of said frame dimensioned to contact the face of the wearer to provide an underwater seal around the eye socket; and a flexible strap secured to the outer end of said frame to extend around the back of the wearer's head to hold the eye pieces in position over the eye sockets, wherein said nose strap includes a plurality of stops divided into two groups of plural stops along the longitudinal axis of the nose strap, the stops of one group being longitudinally spaced apart from each other at a distance different from the distance at which the stops of the other group are spaced from each other, said stops being selectively engageable with said connecting means to space said eye pieces at a desired distance apart from each other.

2. Eye goggles as claimed in claim 1, wherein said stops are projections formed on one surface of said nose strap.

3. Eye goggles as claimed in claim 2, where the length of at least one of said projections is different than the length of said other projections.

4. In eyegoggles comprising a pair of separate eyepieces; a nose strap connecting said eyepieces together; connecting means secured to each eyepiece respectively engaging one of a pair of plural stops formed longitudinally spaced along the nose strap to space the eyepieces a selected distance from each other, the improvement wherein a first pair of adjacent stops are spaced longitudinally from each other by a distance P and a second pair of adjacent stops different from the stops of the first pair are spaced longitudinally from each other by a distance Q, P≠Q, thereby providing a certain number of combinations of the effective length defined between stops engaging the connecting means, said certain number of combinations being greater than the number of combinations of the effective length with P=Q.

5. In eyegoggles comprising a pair of separate eyepieces; a nose strap connecting said eyepieces together; connecting means secured to each eyepiece respectively engaging one of a pair of plural stops formed longitudinally spaced along the strap to space the eyepieces a selected distance from each other, the improvement wherein the length of at least one of said projections is different than the length of said other projection to thereby permit precisional height adjustment of one eyepiece relative to the other eyepiece to occur to accomodate facial contours of the individual wearer.

* * * * *